United States Patent
Prencipe et al.

(10) Patent No.: US 9,655,838 B2
(45) Date of Patent: May 23, 2017

(54) ANTIMICROBIAL COMPOSITIONS COMPRISING ESSENTIAL OIL COMBINATIONS

(71) Applicant: Colgate-Palmolive Company, Piscataway, NJ (US)

(72) Inventors: Michael Prencipe, West Windsor, NJ (US); Shashank Potnis, Maharashtra (IN); Steven Fisher, Middlesex, NJ (US); Navin Lewis, Maharashtra (IN); Gary Tambs, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/783,077

(22) PCT Filed: Jun. 18, 2013

(86) PCT No.: PCT/IN2013/000376
§ 371 (c)(1),
(2) Date: Oct. 7, 2015

(87) PCT Pub. No.: WO2014/203263
PCT Pub. Date: Dec. 24, 2014

(65) Prior Publication Data
US 2016/0051461 A1    Feb. 25, 2016

(51) Int. Cl.
| | | |
|---|---|---|
| A61Q 11/00 | (2006.01) | |
| A61K 8/97 | (2017.01) | |
| A61K 36/53 | (2006.01) | |
| A61K 8/92 | (2006.01) | |
| A61K 8/34 | (2006.01) | |
| A61K 8/33 | (2006.01) | |

(52) U.S. Cl.
CPC ............... *A61K 8/922* (2013.01); *A61K 8/33* (2013.01); *A61K 8/34* (2013.01); *A61K 8/342* (2013.01); *A61K 8/347* (2013.01); *A61Q 11/00* (2013.01)

(58) Field of Classification Search
CPC ........... A61K 2300/00; A61K 2800/92; A61K 36/53; A61K 36/00; A61Q 11/00; A61Q 17/005
See application file for complete search history.

(56) References Cited

U.S. PATENT DOCUMENTS

| | | | |
|---|---|---|---|
| 5,776,435 A | 7/1998 | Gaffar et al. | |
| 6,280,751 B1 | 8/2001 | Fletcher et al. | |
| 6,391,346 B1 | 5/2002 | Newmark et al. | |
| 6,998,112 B2 | 2/2006 | Zuckerman | |
| 2003/0224072 A1 | 12/2003 | Frome | |
| 2004/0253190 A1 | 12/2004 | Maxwell et al. | |
| 2008/0031831 A1 | 2/2008 | Laali | |
| 2011/0059205 A1* | 3/2011 | Gaysinsky | A23G 4/068 426/66 |
| 2012/0039965 A1* | 2/2012 | Van Beek | A01N 65/00 424/400 |
| 2012/0128599 A1 | 5/2012 | Schaeffer-Korbylo et al. | |

FOREIGN PATENT DOCUMENTS

| | | | | |
|---|---|---|---|---|
| FR | 2697133 | | 4/1994 | |
| WO | WO 2011068811 A1 * | | 6/2011 | ............... A61K 8/97 |
| WO | WO 2013066403 | | 5/2013 | |

OTHER PUBLICATIONS

Berlioechi et al., "Toxic profile of bergamot essential oil on survival and proliferation of SH-SY5Y neuroblastoma cells," Food and Chemical Toxicology, Aug. 2011, 49(11):2780-2792.
International Search Report & Written Opinion for International Application No. PCT/IN2013/000376 issued on Sep. 12, 2014.
Katsukawa et al., "Citral, a component of lemongrass oil, activates PPARalpha and gamma and suppresses COX-2 expression," Biochimica and Biophysica Acta. Molecular and Cell Biology of Lipids, Nov. 2010, 1801(11):1214-1220.
Ohloff et al., "The Absolute Configuration of beta-Bisabolol," Helvetica Chimica Acta, 1986, 69:698-703.

* cited by examiner

*Primary Examiner* — Frederick Krass
*Assistant Examiner* — Tracy Liu

(57) ABSTRACT

The invention provides antibacterial combinations of essential oils comprising bisabolol and one or more essential oils selected from citral, carvacrol, oregano extract, and rosemary, or comprising carvacrol and one or more essential oils selected from bisabolol, thymol, and rosemary, together with compositions, e.g., oral care compositions, comprising these combinations, and uses therefore.

6 Claims, No Drawings

ANTIMICROBIAL COMPOSITIONS COMPRISING ESSENTIAL OIL COMBINATIONS

BACKGROUND

Essential oils are volatile oils derived from the leaves, stems, flowers or twigs of plants usually carrying the odor or flavor of the plant. Many essential oils are known to have antimicrobial activity.

For example, bisabolol, or more formally α-(−)-bisabolol (levomenol), is a natural monocyclic sesquiterpene alcohol. It is a colorless viscous oil that is the primary constituent of the essential oil from German chamomile (*Matricaria recutita*) and *Myoporum crassifolium*. It is almost insoluble in water and glycerin, but soluble in ethanol. The enantiomer, α-(+)-bisabolol, is also found naturally but is rare. Synthetic bisabolol ("Syn bisabolol") is usually a racemic mixture of the two, α-(±)-bisabolol.

Another example is carvacrol, or cymophenol, $C_6H_3CH_3(OH)(C_3H_7)$, which is a monoterpenoid phenol. It has a characteristic odor of oregano. Carvacrol is present in the essential oil of *Origanum vulgare* (oregano), oil of thyme, oil obtained from pepperwort, and wild bergamot. The essential oil of Thyme subspecies contains between 5% and 75% of carvacrol, while *Satureja* (savory) subspecies have a content between 1% and 45%. *Origanum majorana* (marjoram) and Dittany of Crete are rich in carvacrol, 50% resp. 60-80%.

The antimicrobial activity of tested essential oils, measured as MIC (Minimum Inhibitory Concentration) is generally low, however, when compared to known antimicrobial agents such as Triclosan and cetyl pyridinium chloride. In many cases, the levels at which these compounds inhibit or kill microorganisms is high enough to present difficulties in formulation, odor, taste, cost and/or efficacy.

Therefore, there is a need for improved formulations comprising essential oils having antimicrobial properties.

SUMMARY OF THE INVENTION

While individual essential oil have limitations on inhibiting microbial growth, a systematic analysis of many combinations shows that some essential oils have much improved activity when combined with a second specific essential oil. Accordingly, at a lower concentration of the individual essential oil, the enhanced activity can be achieved by combining with another essential oil.

The invention thus provides combinations of essential oils having antimicrobial, in particular antibacterial activity, for example bisabolol and one or more essential oils selected from citral, carvacrol, oregano extract, and rosemary, or carvacrol and one or more essential oils selected from bisabolol, thymol, and rosemary. In one embodiment, the combinations are present in an oral care formulation. In another embodiment, the invention provides methods of killing bacteria, or of treating a disease or condition caused by bacterial infection of the oral cavity, for example gingivitis, comprising contacting the affected area with an effective amount of the essential oil combination.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

In a first embodiment, the invention provides an antibacterial combination (Combination 1) comprising bisabolol and one or more essential oils selected from citral, carvacrol, oregano extract, and rosemary, or comprising carvacol and one or more essential oils selected from bisabolol, thymol, and rosemary. For example, the invention provides 1.1. Combination 1 comprising synthetic racemic bisabolol and one or more essential oils selected from citral, carvacrol, oregano extract, and rosemary.

1.2. Composition 1 or 1.1 wherein each of the following ingredients, when present, is present at an amount less than the following levels, e.g. less than or equal to ½ of the following levels, e.g., in an amount for each ingredient of from 10% to 50% of the following levels:
Citral 250 ppm
Thymol 900 ppm
Bisabolol 125 ppm
Rosemary 6000 ppm
Oregano 550 ppm
Carvacrol 80 ppm 1.3. Composition 1 or 1.1 wherein each of the individual essential oils in the composition is present in an amount which is less than half its respective individual minimum inhibitory concentration, e.g., against oral bacteria, e.g., *A. viscosus*.

1.4. Combination 1, 1.1 or 1.2 comprising a combination selected from:
a) Bisabalol 20-50 ppm and Citral 40-100 ppm
b) Bisabolol 50-100 ppm and Carvacrol 30-50 ppm
c) Bisabolol 50-100 ppm and Oregano 250-300 ppm
d) Bisabalol 50-100 ppm and Rosemary 2500-3500 ppm
e) Carvacrol 30-50 ppm and Thymol 400-500 ppm
f) Carvacrol 30-50 ppm and Rosemary 2500-3500 ppm The invention further provides an antibacterial composition comprising any of Combinations 1, et seq. in a carrier medium.

The invention further provides an oral care composition comprising any of Combinations 1, et seq. in an orally acceptable carrier, e.g., in the form of a dentifrice or a mouthwash.

The invention further provides a method of killing or controlling bacteria comprising contacting the bacteria with any of Combination 1, et. seq.

The invention further provides a method of treating or controlling harmful bacteria in the mouth, e.g., treating or controlling gingivitis, comprising administering an effective amount of Combination 1, et seq., e.g., an oral care composition comprising any of Combinations 1, et seq. in an orally acceptable carrier, e.g., in the form of a dentifrice or a mouthwash.

The invention further provides the use of an antibacterial combination (Combination 1) comprising bisabolol and one or more essential oils selected from citral, carvacrol, oregano extract, and rosemary, or comprising carvacrol and one or more essential oils selected from bisabolol, thymol, and rosemary, in the manufacture of a composition to kill or inhibit the growth of bacteria, e.g., to treat or control harmful bacteria in the mouth, e.g., to treat or control gingivitis, As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

In another embodiment of the invention, one or more optional additives can be added to the oral care composition which are include but are not limited to the ingredients described below.

Abrasives

Abrasives may be added to the dentifrice formulation if desired. Any suitable oral care abrasive or polishing agent may be used. Abrasives such as silica, calcined alumina, sodium bicarbonate, calcium carbonate, dicalcium phosphate and calcium pyrophosphate may be included in the base dentifrice compositions used in the practice of the present invention. An embodiment of the abrasives include, but are not limited to, silica abrasives such as precipitated silicas, sodium metaphosphate, potassium metaphosphate, tricalcium phosphate, dihydrated dicalcium phosphate, aluminum silicate, calcined alumina, bentonite or other siliceous materials, particulate thermosetting resins, such as melamine, phenolic, and urea-formaldehydes, and cross-linked polyepoxides and polyesters.

Visually clear dentifrice compositions may be obtained by using an abrasive such as collodial silica, e.g., those sold under the trade designation Zeodent 115 available from the Huber Corporation or alkali metal aluminosilicate complexes (that is, silica containing alumina combined in its matrix) which have refractive indices close to the refractive indices of gelling agent-liquid (including water and/or humectant) systems used in dentifrice compositions.

Anti-Bacterial Agents

Optional additivess include additional antimicrobial (e.g., antibacterial) agents. Any orally acceptable antimicrobial agent can be used, including Triclosan (5-chloro-2-(2,4-dichlorophenoxy)phenol); 8-hydroxyquinoline and salts thereof, zinc and stannous ion sources such as zinc citrate, zinc sulphate, zinc glycinate, sodium zinc citrate and stannous pyrophosphate; copper (II) compounds such as copper (II) chloride, fluoride, sulfate and hydroxide; phthalic acid and salts thereof such as magnesium monopotassium phthalate; sanguinarine; quaternary ammonium compounds, such as alkylpyridinium chlorides (e.g., cetylpyridinium chloride (CPC), combinations of CPC with zinc and/or enzymes, tetradecylpyridinium chloride, and N-tetradecyl-4-ethyl-pyridinium chloride); bisguanides, such as chlorhexidine digluconate, hexetidine, octenidine, alexidine; halogenated bisphenolic compounds, such as 2,2' methylenebis-(4-chloro-6-bromophenol); benzalkonium chloride; salicylanilide, domiphen bromide; iodine; sulfonamides; bisbiguanides; phenolics; piperidino derivatives such as delmopinol and octapinol; magnolia extract; grapeseed extract; thymol; eugenol; menthol; geraniol; carvacrol; citral; eucalyptol; catechol; 4-allylcatechol; hexyl resorcinol; methyl salicylate; antibiotics such as augmentin, amoxicillin, tetracycline, doxycycline, minocycline, metronidazole, neomycin, kanamycin and: clindainycin; and mixtures thereof. A further illustrative list of useful antibacterial agents is provided in U.S. Pat. No. 5,776,435, Gaffar, et al., issued Jul. 7, 1998. In some embodiments, the antimicrobial agent is present at a concentration of from about 0.001 to about 1%, by weight. In some embodiments, the antimicrobial agent is cetylpyridinium chloride. In some embodiments, cetylpyridinium chloride is present at a concentration of from about 0.001 to about 1%, by weight. In other embodiments, cetylpyridinium chloride is present at a concentration of about 0.05%, by weight.

Anti-Oxidants

Antioxidants are another class of optional additives. Any Orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

Anti-Plaque Agents

Optionally, an antiplaque (e.g., plaque disrupting) agent may be included. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium Polyacrylates and Mixtures Thereof.

Breath Freshening Agents

Optionally, breath freshening agents may be provided. Any orally acceptable breath freshening agent can be used, including without limitation zinc salts such as zinc gluconate, zinc citrate and zinc chlorite, alpha-ionone and mixtures thereof. One or more breath freshening agents are optionally present in a breath freshening effective total amount.

Desensitizing Agents

Optional desensitizing agents include potassium citrate, potassium chloride, potassium tartrate, potassium bicarbonate, potassium oxalate, potassium nitrate, strontium salts, and mixtures thereof.

Fluoride Ion Source

Some embodiments provide compositions wherein at least one of the one or more components is a fluoride ion source selected from: stannous fluoride, sodium fluoride, potassium fluoride, sodium monofluorophosphate, sodium fluorosilicate, ammonium fluorosilicate, amine fluoride, ammonium fluoride, and a combination of two or more thereof.

Unless otherwise specified, all percentages and amounts expressed herein and elsewhere in the specification should be understood to refer to percentages by weight. The amounts given are based on the active weight of the material.

Stannous Ion Source

Optionally, a stannous ion source may be included, for example, as a periodontal active, tartar control agent, anti-caries agent or tooth desensitizer. Any orally acceptable stannous ion Source can be used, including stannous fluoride, other stannous halides such as stannous chloride dihydrate, organic stannous carboxylate salts such as stannous formate, acetate, gluconate, lactate, tartrate, oxalate, malonate and citrate, stannous ethylene glyoxide and the like.

Tartar Control Agents

Optionally, the composition may include a tartar control (anticalculus) agent. Tartar control agents among those useful herein include phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-d iphosphonie acid (EHDP) and ethane-1-amino-1,1-diphosphonate, phosphonoalkane carboxylic acids and, salts of any of these agents, for example their alkali metal and ammonium salts. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof, wherein sodium can optionally be replaced by potassium or ammonium. Other useful anticalculus agents include polycarboxylate polymers and polyvinyl methyl ether/maleic anhydride (PVME/MA) copolymers, such as those available under the Gantrez™ brand from ISP, Wayne, N.J. In some embodiments, a phosphate is present at a concentration of from about 0.01 to about 10%, by weight. In some embodiments, a phosphate is present at a concentration of from about 1%, by weight.

Whitening Agents

Optionally, the composition may include a whitening agent. Whitening agents, material which is effective to effect whitening of a tooth surface to which it is applied, such as hydrogen peroxide and urea peroxide, high cleaning silica, preservatives, silicones, and chlorophyll compounds may be incorporated into the compositions of the present invention. In various embodiments, the compositions of this invention comprise a peroxide whitening agent, comprising a peroxide compound. A peroxide compound is an oxidizing compound comprising a bivalent oxygen-oxygen group. Peroxide compounds include peroxides and hydroperoxides, such as hydrogen peroxide, peroxides of alkali and alkaline earth metals, organic peroxy compounds, peroxy acids, pharmaceutically-acceptable salts thereof, and mixtures thereof. Peroxides of alkali and alkaline earth metals include lithium peroxide, potassium peroxide, sodium peroxide, magnesium peroxide, calcium peroxide, barium peroxide, and mixtures thereof. Organic peroxy compounds include carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, and monoperoxyphthalate, and mixtures thereof. Peroxy acids and their salts include organic peroxy acids such as alkyl peroxy acids, and monoperoxyphthalate and mixtures thereof, as well as inorganic peroxy acid salts such as persulfate, dipersulfate, percarbonate, perphosphate, perborate and persilicate salts of alkali and alkaline earth metals such as lithium, potassium, sodium, magnesium, calcium and barium, and mixtures thereof. In various embodiments, the peroxide compound comprises hydrogen peroxide, urea peroxide, sodium percarbonate and mixtures thereof. In some embodiments, the peroxide compound comprises hydrogen peroxide. In some embodiments, the peroxide compound consists essentially of hydrogen peroxide. In some embodiments a non-peroxide whitening agent may be provided. Whitening agents among those useful herein include non-peroxy compounds, such as chlorine dioxide, chlorites and hypochlorites. Chlorites and hypochlorites include those of alkali and alkaline earth metals such as lithium, potassium, sodium, magnesium, calcium and barium. Non-peroxide whitening agents also include colorants, such as titanium dioxide and hydroxyapatite. One or more whitening agents are optionally present in a tooth-whitening effective total amount. In some embodiments the whitening agent is separated from the aqueous carrier. In some embodiments the whitening agent is separated from the aqueous carrier by encapsulation of the whitening agent.

Zinc Salts

Optionally, the composition may include a zinc salt which include, but is not limited to zinc acetate, zinc borate, zinc butyrate, zinc carbonate, zinc citrate, zinc formate, zinc gluconate, zinc glycerate, zinc glycolate, zinc lactate, zinc oxide, zinc phosphate, zinc picolinate, zinc proprionate, zinc salicylate, zinc silicate, zinc stearate, zinc tartrate, zinc undecylenate and mixtures thereof.

Other Additives

As desired, any other additives may be included in the dentifrice composition for reasons of e.g., manufacturing, stability, aesthetics, therapeutic effect, consumer appeal, etc. Exemplary additives include all other conventional dentifrice additives, viscosity modifiers, diluents, foam modulators, saliva stimulating agents, desensitizing agents, whitening agents, enzymes, pH modifying agents, mouth-feel agents, sweeteners, colorants, opacifiers, and breath freshening agents. Exemplary additives include, but are not limited to those agents cited in the International Cosmetic. Ingredient Dictionary and Handbook, 14$^{th}$ Edition (2012), which is incorporated herein by reference.

EXAMPLES

Embodiments of the present invention are further described in the following examples. The examples are merely illustrative and do not in any way limit the scope of the invention as described and claimed.

Example 1

Determination of MIC of Individual Essential Oils

Minimum inhibitory concentration (MIC) is assessed as follows: A 96-well microtiter plate is inoculated with 100 µl of TSB (Tryptic Soy Broth) media in each well. Stock solutions of the active are prepared as required (w/v basis) in percent. The different stock solutions (>1%) are used to achieve the final MIC concentration of the actives. The positive control (Triclosan) is prepared as a 0.1% stock solution. Each active is diluted 1:10 using sterile TSB. 100 µl of the stock solution is added in the first column for the actives and the controls. Transfer 100 µl of the solution from the first column to the next, mix and repeat the transfer to serially dilute 2-fold across the plate. The last 100 µl is discarded. Prepare 0.2-0.3 O.D. activated culture of *A. viscosus* ATCC 43146 grown in TSB overnight at 37° C. Add 100 µl of the adjusted bacterial culture to each well. Incubate the plates for 24 hours at 37° C. Determine the growth by measuring the O.D. at 610 nm. The data is transferred to an Excel spreadsheet for comparison of the O.D. values. The concentration higher than the lowest concentration with large increment in O.D. is taken as the MIC. Depending on the value obtained the MIC is repeated using higher or lower concentrations of the stock solution. This gives the closest value of the concentration determined by serial dilution at which the microorganism is inhibited (MIC).

TABLE 1

MIC values of individual essential oils against *A. viscosus*

| Essential oil | MIC value (ppm) |
| --- | --- |
| Eugenol | 2000 |
| Dihydro-eugenol | 500 |
| Methyl salicylate | 1000 |
| Citral | 250 |
| Eucalyptol | 250 |
| Thymol (98% pure) | 900 |
| Neem oil | 100 |

TABLE 1-continued

MIC values of individual essential oils against *A. viscosus*

| Essential oil | MIC value (ppm) |
|---|---|
| Benzyl alcohol | 700 |
| Syn. Bisabolol | 125 |
| Catechins hydrate | 100 |
| Rosemary | 6000 |
| Parsely | 4000 |
| Oregano | 550 |
| Cavarcrol | 80 |
| Green tea catechin | 80 |
| Ginger | 625 |
| Zinc oxide | 625 |
| Zinc citrate | 160 |
| IPMP (99.8% pure) | 160 |

Example 2

Determination of Activity of Essential Oil Combinations

Minimum inhibitory concentration (MIC) of combinations of the above actives is assessed as follows: A 96 well microtiter plate is dispensed with 100 μl of growth medium in each well using a 8 channel micropipettor. Prepare stock solution of active to be tested in appropriate solvent. Minimum inhibitory concentration is chosen as the starting point. Dilute each of the actives, positive and solvent control in the growth medium (1 ml of active stock+9 ml of TSB). Also dilute each of the active solution in TSB as (1 ml of active '1'+1 ml of active '2'+8 ml of TSB) to get a combination solution of the active. To the wells of the first column add 100 μl ethanol diluted (1:9) in growth medium (1A and 1B). Active 1 diluted in growth medium (1C and 1D), Active 2 diluted in growth medium (1E and 1F), combination of actives diluted in growth medium (1G and 1H). Each of the wells in the first column has now 200 μl of solution. Using a 8 channel multipipettor, mix in the well this 200 μl solution and then transfer 100 μl to the wells in the next column, mix again these solutions in the second column and transfer 100 μl to the next columns. This procedure is repeated from all 12 columns after which 100 μl from each well in column should be discarded. This allows us to obtain a gradient of actives in each well with a sequential 2 fold dilution starting at minimum inhibitory concentration in the first well all the way on the left side of the plate. Take overnight bacterial growth culture and Gram stain to check purity. If the culture is pure proceed with the next step. Measure OD at 610 nm of the overnight culture in the spectrophotometer. Dilute the overnight culture using the appropriate growth medium (TSB for *A. viscosus*) to an OD 610 nm of about 0.2. 100 μl of bacterial culture adjusted in growth medium to OD at 610 nm of 0.2 is then added to each well. Each well on the plate now has a total volume of 200 μl. The plates are incubated with the microtiter plate lid on at 37 C. for 12-16 for aerobic bacteria. The growth is measured by measuring turbidity in each well using microtiter plate reader. Tabulate the values in an Excel spreadsheet and observe for change in OD value over the dilution. The higher of the concentration showing no growth is taken as the inhibitory concentration. If the combination of the active shows an inhibitory concentration below the MIC value of individual MIC values of actives the combination is considered for antimicrobial (antibacterial) action.

Combinations of essential oils are set forth in Table 2 below. (Syn Bisabolol=synthetic bisabolol)

TABLE 2

Values of inhibition concentration of various combinations of essential oils

| Ingredient combination | MIC value resulting in synergy |
|---|---|
| Syn Bisabolol + Citral | Syn Bis 31.25 ppm + Citral 62.5 ppm |
| Syn Bisabolol + Carvacrol | Syn Bis 62.5 ppm + Carvacrol 40 ppm |
| Syn Bisabolol + Oregano | Syn Bis 62.5 ppm + Oregano 275 ppm |
| Syn Bisabolol + Rosemary | Syn Bis 62.5 ppm + Rosemary 3000 ppm |
| Carvacrol + Thymol | Carvacrol 40 ppm + Thymol 450 ppm |
| Carvacrol + Rosemary | Carvacrol 40 ppm + Rosemary 3000 ppm |

The combinations of essential oils from Table 2 were also compared against the concentration of each essential oil alone necessary to product the same effect. These values are disclosed in Table 3 below.

TABLE 3

Values of individual MIC with various combinations of essential oils

| | |
|---|---|
| Syn Bisabolol + Citral | Syn Bis 31.25 ppm + Citral 62.5 ppm |
| Syn Bisabolol | 125 ppm |
| Citral | 250 ppm |
| Syn Bisabolol + Carvacrol | Syn Bis 62.5 ppm + Carvacrol 40 ppm |
| Syn Bisabolol | 125 ppm |
| Carvacrol | 80 ppm |
| Syn Bisabolol + Oregano | Syn Bis 62.5 ppm + Oregano 275 ppm |
| Syn Bisabolol | 125 ppm |
| Oregano | 550 ppm |
| Syn Bisabolol + Rosemary | Syn Bis 62.5 ppm + Rosemary 3000 ppm |
| Syn Bisabolol | 125 ppm |
| Rosemary | 6000 ppm |
| Carvacrol + Thymol | Carvacrol 40 ppm + Thymol 450 ppm |
| Carvacrol | 80 ppm |
| Thymol | 900 ppm |
| Carvacrol + Rosemary | Carvacrol 40 ppm + Rosemary 3000 ppm |
| Carvacrol | 80 ppm |
| Rosemary | 6000 ppm |

As can be seen from the above data, the amount of essential oil can be greatly reduced in the composition of the invention.

These results show that combinations of specific essential oils complement each other with synergistic effect on antimicrobial efficacy as reflected in the MIC values.

As those skilled in the art will appreciate, numerous changes and modifications may be made to the embodiments described herein without departing from the spirit of the invention. It is intended that all such variations fall within the scope of the appended claims.

We claim:

1. An antibacterial combination of essential oils comprising carvacrol and one or more essential oils selected from, thymol and rosemary; wherein the combination comprises essential oils in amounts selected from:
   a) Carvacrol 30-50 ppm and Thymol 400-500 ppm
   b) Carvacrol 30-50 ppm and Rosemary 2500-3500 ppm.

2. The antibacterial combination of claim 1 wherein each of the individual essential oils in the combination is present in an amount which is less than half its respective individual minimum inhibitory concentration.

3. An antibacterial composition comprising the antibacterial combination of claim 1 in a carrier medium.

4. An oral care composition comprising the antibacterial combination of claim 1 in an orally acceptable carrier.

5. A method of killing or controlling bacteria comprising contacting the bacteria with the antibacterial combination of claim 1.

6. A method of treating, or controlling harmful bacteria in the mouth comprising administering an effective amount an oral care composition according to claim 4 to the mouth of a subject in need thereof.

* * * * *